United States Patent [19]

Bertland et al.

[11] 4,017,360

[45] Apr. 12, 1977

[54] METHOD FOR PURIFYING HEPATITIS B ANTIGEN

[75] Inventors: Alexander U. Bertland; Alfred A. Tytell, both of Lansdale; George P. Lampson, Hatfield; Eugene Buynak, North Wales, all of Pa.

[73] Assignee: Merck & Co., Inc., Rahway, N.J.

[22] Filed: May 14, 1975

[21] Appl. No.: 577,483

[52] U.S. Cl. .................................. 195/1.4; 195/1.5; 424/89
[51] Int. Cl.² .................. A61K 39/12; C12K 5/00; C12K 7/00
[58] Field of Search ................ 424/89; 195/1.4, 1.5

[56] References Cited

UNITED STATES PATENTS 3,636,191   1/1972   Blumberg ........................... 424/89

OTHER PUBLICATIONS

Houwen et al.–Chem. Abst. vol. 79 (1973) p. 64320t.
Geserick et al.–Chem. Abst. vol. 81 (1974) p. 36325w.

*Primary Examiner*—Sam Rosen
*Attorney, Agent, or Firm*—Donald J. Perrella; J. Jerome Behan

[57] ABSTRACT

Hepatitis B antigen useful as vaccine is prepared from clarified plasma of hepatitis B donors by treating with pepsin at a pH wherein pepsin is enzymatically active, treating with urea, and optionally treating with formaldehyde.

7 Claims, 1 Drawing Figure

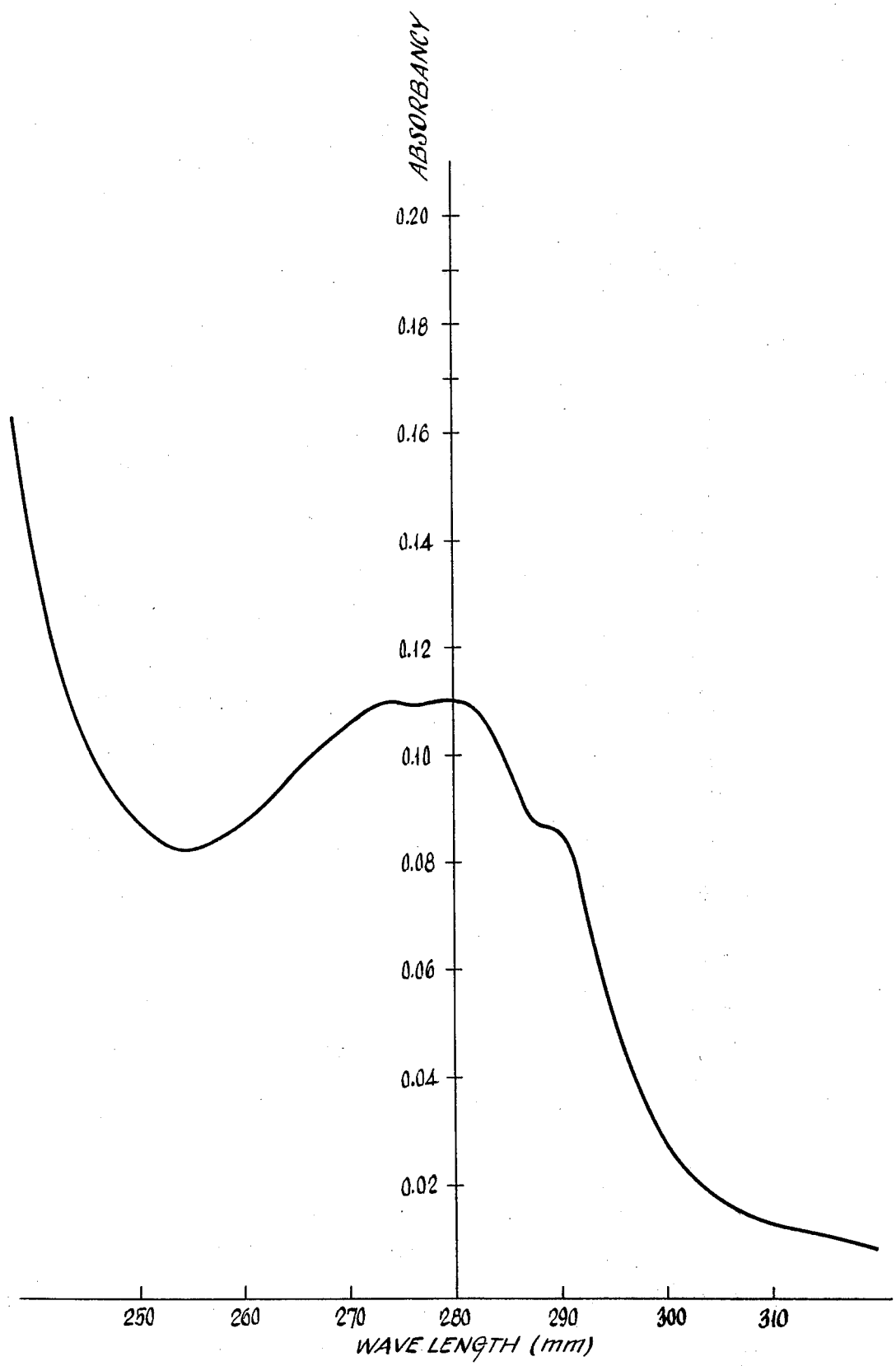

METHOD FOR PURIFYING HEPATITIS B ANTIGEN

BACKGROUND OF THE INVENTION

This invention relates to hepatitis B and, more particularly, to a vaccine for hepatitis B and to a method for purifying hepatitis B antigen for use as a vaccine.

Hepatitis B is one of two types of viral hepatitis which results in a systemic infection with the principal pathologic changes occurring in the liver. This disease affects mainly adults and is maintained chiefly by transfer of infection from long term carriers of the virus. Usual methods of spread are by blood transfusion, contaminated needles and syringes, through skin breached by cuts or scratches, by unsterilized dental instruments as well as by saliva, venereal contact or exposure to aerosolized infected blood.

The incubation period of type B hepatitis is relatively long: from 6 weeks to 6 months may elapse between infection and the onset of clinical symptoms. The illness usually begins with fatigue and anorexia, sometimes accompanied by myalgia and abdominal discomfort. Later jaundice, dark urine, light stools and tender hepatomegaly may appear. In some cases, the onset may be rapid, with appearance of jaundice early in association with fever, chills and leukocytosis. In other cases, jaundice may never be recognized and the patient may be aware only of a "flu-like" illness. It is estimated that the majority of hepatitis infections result in a mild, anicteric illness.

Although qualitatively similar to viral hepatitis A, the disease is readily diagnosed by the appearance of the Australia antigen particles, now designated by $HB_sAg$ (surface antigen), in the blood or other clinical specimens (saliva, urine, bile, feces). There occurs in the blood of infected individuals a relatively large population ($10^{14}$–$10^{15}$/ml.) of spherical particles. The particles are 18–22 nm in diameter and have the same antigenic determinants as the surface of the 42 nm Dane particle which may be the virus of hepatitis B, now designated HBV.

U.S. Pat. No. 3,735,004 indicates that boiled infectious serum was used to vaccinate children with resulting antibody to $HB_sAg$ (anti-$HB_s$) and that such serum provided protection against challenge. The dose of boiled serum used was equivalent to about $1 \times 10^{12}$ $HB_s$ particles. The recipients of such serum did not develop clinical or bio chemical disease. This serum, however, is not suitable for use as a vaccine, because of its impure nature, its lack of reproducibility and its non-quantitation.

It is, accordingly, an object of the present invention to provide a vaccine for hepatitis B. Another object is to purify hepatitis B antigen by removing extraneous undesirable proteins and/or antigens. A further object is to provide a method for removing extraneous undesirable proteins or antigens from hepatitis B antigen. Yet another object is to provide pharmaceutical preparations to administer the purified hepatitis B antigen as a vaccine. These and other objects of the present invention will be apparent from the following description.

SUMMARY OF THE INVENTION

Partially purified concentrate from clarified plasma containing hepatitis B antigen is subjected to the following sequence of operations:

1. the concentrate is treated with pepsin at a pH in the range wherein pepsin is active;
2. the concentrate is treated with urea; and
3. the concentrate optionally is treated with formaldehyde.

The resulting product, a highly purified, reproducible, characterizable hepatitis B antigen separated from extraneous undesirable proteins and/or antigens, is useful as a vaccine.

BRIEF DESCRIPTION OF THE DRAWING

The drawing is an ultra-violet spectrum of the antigen of the invention.

DETAILED DESCRIPTION

The starting material for the purified hepatitis B surface antigen ($HB_sAg$) of the present invention is plasma obtained from donors, e.g., by plasmaphoresis. The level of antigen may be measured in known manner by radioimmune assay, passive hemagglutination or complement fixation. The plasma is cooled and the cryoprecipitate which forms is removed by light centrifugation. The remaining clarified plasma containing $HB_sAG$ is concentrated by one or more techniques, e.g. isopycnic banding, rate zonal banding or precipitation, e.g. by means of polyethylene glycol, ammonium sulfate, sodium sulfate, and the like. This partially purified concentrate is the starting material for the present invention.

In isopycnic banding the partially purified concentrate is contacted with a liquid medium having a density gradient therein which includes the density of the specific antigen required. The liquid medium is then subjected to ultracentrifugation to attain an equilibrium distribution of the serum components through the density gradient, according to their individual densities. Successive fractions of the medium are then displaced and those containing the desired antigen are then separated. The application of this technique to the purification of Australia antigen is described in German Specification No. 2,049,515 and U.S. Pat. No. 3,636,191.

In rate zonal banding the partially purified concentrate is subjected to ultracentrifugation in contact with a liquid medium having a density gradient therein, but this time using the rate zonal technique, i.e. at a rate and for a period such that equilibrium is not attained, the $HB_sAg$ and other residual serum components being distributed through the medium according to their sedimentation coefficients in the medium.

The liquid media used in the process may be any density gradient in the appropriate ranges. Suitable solutes for such solutions include, e.g. sucrose, potassium bromide, cesium chloride, sodium bromide, potassium tartrate and the like. The isopycnic banding step is conveniently carried out in a centrifuge, for example, Electronucleonics-K, by filling the stationary rotor with saline solution, then successively displacing the saline solution upwards with aliquots of a liquid medium solution of increasing density until a step gradient is formed.

The plasma is introduced at the top of the rotor displacing some of the highest density solution from the bottom. The centrifuge is brought up to speed through a programmed speed control system which prevents mixing during the initial reorientation phase. When equilibrium is attained and the product is in its proper density position, the rotor is slowed down through the same system to prevent mixing upon reorientation to the original configuration. Then the gradient is drained from below and the proper density cut collected. A similar technique is used in the rate zonal banding. The proper density cut from this banding is the partially purified concentrate of hepatitis B antigen.

The protein concentration of the partially purified concentrate is then adjusted to from about 40 to about 200 micrograms per ml. by addition of sterile, pyrogen-free phosphate buffered saline (PBS). The solution is then acidified to from about pH 2 to about pH 4, preferably with HCl at about 25° C.

A solution of purified pepsin in water, preferably prepared from crystalline pepsin, is added so that the solution contains about 1 microgram of pepsin per from about 40 to about 500 micrograms of protein. The solution is incubated until digestion of the extraneous protein by the pepsin is complete, typically in from about 8 to about 24 hours at a temperature of about 30° C. to about 38° C. The solution is then brought to about pH 7 by addition of a base, e.g. NaOH. The pepsin digested material is concentrated by ultrafiltration at about 5° C. and urea is added (preferably highly purified crystalline grade) until the final concentration is effective to dissociate proteinaceous matter, typically from about 4M to about 8M. The mixture is then incubated at elevated temperature, typically at from about 30° C. to about 38° C. for from about 16 to about 24 hours to effect further purification.

The incubated mixture is clarified by filtration and chromatographed on a column to remove urea, pepsin and remnants of pepsin digestion. The column is eluted with a sterile, pyrogen-free physiologically acceptable buffer which is compatable with the column, e.g. PBS, a mixture of $NaH_2PO_4$ and $Na_2HPO_4$ or tris. Fractions determined to contain $HB_sAg$ by known methods, e.g. radioimmune assay, complement fixation and ultraviolet spectrophotometry, are pooled and diluted to a level of about 20 micrograms $HB_sAg$ per ml. with sterile, pyrogen-free physiologically acceptable buffer, (some examples of which have been given above). The diluted pooled fractions are sterile filtered. To the filtered batch formaldehyde is optionally added at a concentration known to inactivate viruses, e.g. from about 50 to about 200 micrograms per ml. The mixture is then incubated at from about 30° C. to about 38° C. for from about 50 to about 100 hours. A sterile solution of a physiologically acceptable neutralizing agent, e.g. $NaHSO_3$, is added to substantially neutralize the formaldehyde. The material is dispensed aseptically into glass vials and stored for future use.

The purified hepatitis B surface antigen of the present invention is a highly purified, reproducible product and characterized in having a particle size diameter of from about 18 to about 22 nm, an $E_{278nm}$ 1% typically from about 52 to about 54, and a UV spectrum as shown in FIG. 1.

The accompanying drawing is an ultraviolet spectrum of the purified Hepatitis B antigen of the present invention.

The following examples illustrate the present invention without, however, limiting the same thereto.

EXAMPLE 1

The rotor of a centrifuge, Electronucleonics K, is filled with 8,400 ml of phosphate buffer. After running the rotor up to 10,000 rpm to degas the system, the following step gradient is pumped into the bottom of the stationary rotor:

1. 2,400 ml of 10% NaBr, $\rho = 1.08$
2. 1,000 ml of 20% NaBr, $\rho = 1.17$
3. 1,500 ml of 30% NaBr, $\rho = 1.28$
4. 3,500 ml of 40% NaBr, $\rho = 1.41$ Plasma containing Australia antigen, 1,750 ml is pumped into the top of the stationary rotor displacing 1,750 ml of 40% NaBr from the bottom of the rotor. The rotor is accelerated to 30,000 rpm and run at this speed for 4 hours. The rotor is then stopped and 1,750 ml of 40% NaBr are pumped into the bottom of the rotor forcing the plasma out the top. An additional 1,750 ml of fresh plasma containing Australia antigen are pumped into the top of the rotor displacing an equal volume of 40% NaBr out the bottom of the rotor. The rotor is then run at 30,000 rpm for 18 hours. After stopping the rotor the $HB_sAg$ rich material in the 1.21 − 1.24 density region, 1,000 ml, is collected and dialyzed against phosphate buffer.

The rotor is then filled with phosphate buffer, degassed as above, and the following step gradient pumped into the bottom of the stationary rotor:

1. 2,400 ml of 5% sucrose, $\rho = 1.02$
2. 1,750 ml of 15% sucrose, $\rho = 1.06$
3. 1,750 ml of 25% sucrose, $\rho = 1.10$
4. 2,500 ml of 50% sucrose, $\rho = 1.23$ The $HB_sAg$ rich material from the NaBr isopycnic banding step, 1,000 ml, is pumped into the rotor top displacing 1,000 ml. of 50% sucrose out the rotor bottom. The rotor is then run at 28,000 rpm for 18 hours. After stopping the rotor the $HB_sAg$ rich material in the 1.135 − 1.165 density region, 1,000 ml, is collected. This product is then diluted to 40 micrograms protein per milliliter to yield 56 liters of material. The diluent is phosphate buffered saline. The 56-liter batch of zonal centrifuge partially purified hepatitis B antigen ($HB_sAg$) at 40µg/ml is acidified to pH 2 at room temperature by the addition of one normal hydrochloric acid with stirring. 56 ml of a 1 mg/ml solution of crystalline pepsin in distilled water is added. The final concentration of pepsin was 1 µg/ml. The $HB_sAg$ batch is incubated 16 hours at 37° C. and neutralized to pH 7 by the addition of one normal sodium hydroxide.

The pepsin-digested batch is concentrated 295-fold by ultrafiltration using an Amicon apparatus equipped with an XM100A membrane. Pepsin degraded non-antigen protein passes through the membrane into the ultrafiltrate but $HB_sAg$ particles are retained.

Solid urea is added to the concentrate to make a 4–8 molar urea solution which is then incubated another 16 hours at 37° C. The urea-treated $HB_sAg$ concentrate is clarified by filtration through a fiberglass filter and chromatographed on Sephadex G-150. The antigen is eluted at the void volume and is free from urea, pepsin and other protein impurities. The fraction containing purified $HB_sAg$ is diluted to a use level and sterile filtered. Formalin is added to a concentration of 90–100 µg/ml for 72 hours at 36° C to further insure against the possibility of the presence of infectious viruses. At the end of formalin treatment, excess formaldehyde is neutralized with sodium bisulfite. The purified product has an $E_1$% of 52.3 compared to an $E_1$% of 23.8 for the zonal centrifugation starting material. The purified product consists of spherical particles having a diameter of from 18–22 nm and UV spectrum as shown in the accompanying drawing.

A summary of purification, biological and physical properties are shown in the following table.

|                          | Zonal Centri-fugation Product | Final Product |
|--------------------------|-------------------------------|---------------|
| OD$_{280nm}$             | 0.095                         | 0.115         |
| OD$_{260nm}$             | 0.085                         | 0.082         |
| Volume (ml)              | 56,000                        | 23,300        |
| TOTAL OD$_{280nm}$       | 5,320                         | 2,680         |
| Lowry Protein (µg/ml)    | 40.0                          | 22.0          |
| Total Protein (mg)       | 2,240                         | 513           |
| % Protein Removal        | —                             | 77            |
| CF Units per ml.         | 64                            | 128           |
| Total CF Units           | 3,584,000                     | 2,982,000     |
| % Yield in CF            | —                             | 83            |
| CF Units per µg/ml Protein | 1.6                         | 5.8           |
| RIA Units/ml             | 2,000                         | 8,000         |
| TOTAL RIA Units          | 112,000,000                   | 180,000,000   |
| % Yield in RIA           | —                             | 160           |
| RIA Units per µg Protein | 50                            | 364           |

EXAMPLE 2

When injected subcutaneously with a single dose (1.0 ml.) containing 20 micrograms of the hepatitis B surface antigen of the present invention, four out of a group of six chimpanzees developed antibodies. After two similar additional doses at four-week intervals, five of the six chimpanzees had developed antibodies.

EXAMPLE 3

Sixteen chimpanzees were divided into three groups. Group A (six chimpanzees) was inoculated intravenously with 1.0 ml. of BOB hepatitis B virus; Group B (four chimpanzees) was inoculated intravenously with 1.0 ml. of the hepatitis B surface antigen of the present invention; Group C (six chimpanzees) was the control group and received no inoculation. All chimpanzees of Group A had evidence of clinical hepatitis B infection (either antigenemia, enzyme elevations and/or antibody response) within forty weeks. None of the chimpanzees of Group B or C showed evidence of clinical hepatitis B infection over the same forty-week period.

EXAMPLE 4

Three groups of grivet monkeys (six monkeys in each group) were given 3 injections subcutaneously at four-week intervals with 1.0 ml. doses containing varying amounts of the antigen of the present invention. The following table shows the dosage administered to each group in each injection and the number of animals out of the total in that group showing antibody formation prior to the next injection, or within 4 weeks following the last injection.

| Group | Vaccine Dose (µg/ml) | No. of Animals Showing Antibody Response |        |        |
|-------|----------------------|------------------------------------------|--------|--------|
|       |                      | Week 0                                   | Week 4 | Week 8 |
| A     | 20                   | 2/6                                      | 2/6    | 5/6    |
| B     | 2                    | 0/6                                      | 1/6    | 4/6    |
| C     | 0.5                  | 0/6                                      | 1/6    | 2/6    |

Significantly, more than 50% of the animals showed an antibody response after three doses of vaccine at a dosage level of 2 micrograms.

EXAMPLE 5

Three groups of guinea pigs (14 in each group) were injected subcutaneously at 0, 14 and 56 day intervals with 1.0 ml. doses containing varying amounts of the antigen of the present invention. The following table shows the dosage administered to each group, each injection and the number of animals out of the total in that group showing antibody formation when tested on day 0, 28, 56 and 84.

| Group | Vaccine Dose (µg/ml) | No. of Animals Showing Antibody Response |        |        |        |
|-------|----------------------|------------------------------------------|--------|--------|--------|
|       |                      | Day 0                                    | Day 28 | Day 56 | Day 84 |
| A     | 20                   | 0/14                                     | 12/14  | 10/11  | 10/10  |
| B     | 2                    | 0/14                                     | 7/14   | 4/11   | 10/10  |
| C     | 0.5                  | 0/14                                     | 2/14   | 3/14   | 10/12  |

Significantly, over 80% of the guinea pigs showed antibody formation after three doses of vaccine at a dosage level of 0.5 microgram.

What is claimed is:

1. A method for purifying hepatitis B antigen from a partially purified concentrate obtained from clarified plasma containing hepatitis B antigen comprising treating the concentrate with a quantity of pepsin effective to digest proteinaceous matter at a pH within the range wherein pepsin is enzymatically active, treating the concentrate with a quantity of urea effective to dissociate proteinaceous matter, and removing pepsin, pepsin degradation products and urea, and optionally adding formaldehyde in a concentration effective to inactivate viruses.

2. A method according to claim 1 wherein the pH of the concentrate is adjusted to about 2 with HCl.

3. A method according to claim 1 wherein the pepsin is added until its concentration is about 1 microgram/ml. per from about 40 to about 500 micrograms of protein.

4. A method according to claim 1 wherein urea is added until its concentration is from about 4M to about 8M.

5. A method according to claim 1 wherein formaldehyde is added following removal of pepsin, pepsin degradation products and urea.

6. A method according to claim 5 wherein the formaldehyde is added until its concentration is from about 50 to about 200 micrograms/ml.

7. A method according to claim 5 wherein removal is effected by filtration and chromatography.

* * * * *